United States Patent
Dashti et al.

(10) Patent No.: US 11,311,650 B2
(45) Date of Patent: Apr. 26, 2022

(54) DEVICES FOR SUPPORTING REGENERATION OF BODY TISSUES, AND METHODS OF MAKING AND USING THEM

(71) Applicants: The Administrators of the Tulane Educational Fund, New Orleans, LA (US); Nanofibers Solutions, LLC, Dublin, OH (US); Ruth Waterman, San Diego, CA (US)

(72) Inventors: Derek C. Dashti, Canyon Country, CA (US); Aline M. Betancourt, San Diego, CA (US); Jed Johnson, Columbus, OH (US); Ruth Waterman, San Diego, CA (US)

(73) Assignees: The Administrators of the Tulane Educational Fund, New Orleans, LA (US); Nanofiber Solutions, LLC, Dublin, OH (US)

( * ) Notice: Subject to any disclaimer, the term of this patent is extended or adjusted under 35 U.S.C. 154(b) by 190 days.

(21) Appl. No.: 15/764,099

(22) PCT Filed: Sep. 30, 2016

(86) PCT No.: PCT/US2016/055035
§ 371 (c)(1),
(2) Date: Mar. 28, 2018

(87) PCT Pub. No.: WO2017/059377
PCT Pub. Date: Apr. 6, 2017

(65) Prior Publication Data
US 2018/0272037 A1    Sep. 27, 2018

Related U.S. Application Data

(60) Provisional application No. 62/234,744, filed on Sep. 30, 2015.

(51) Int. Cl.
| | | |
|---|---|---|
| *A61L 27/26* | (2006.01) | |
| *A61L 27/54* | (2006.01) | |
| *A61L 27/56* | (2006.01) | |
| *A61L 27/36* | (2006.01) | |
| *D04H 1/728* | (2012.01) | |
| *A61L 27/18* | (2006.01) | |
| *A61L 27/20* | (2006.01) | |
| *A61L 27/58* | (2006.01) | |
| *A61K 39/39* | (2006.01) | |
| *A61L 27/38* | (2006.01) | |
| *C12N 5/0775* | (2010.01) | |
| *D04H 3/011* | (2012.01) | |
| *A61K 39/00* | (2006.01) | |

(52) U.S. Cl.
CPC .......... *A61L 27/3691* (2013.01); *A61K 39/39* (2013.01); *A61L 27/18* (2013.01); *A61L 27/20* (2013.01); *A61L 27/26* (2013.01); *A61L 27/3834* (2013.01); *A61L 27/54* (2013.01); *A61L 27/56* (2013.01); *A61L 27/58* (2013.01); *C12N 5/0668* (2013.01); *D04H 1/728* (2013.01); *D04H 3/011* (2013.01); *A61K 2039/55561* (2013.01); *A61L 2300/41* (2013.01); *A61L 2400/12* (2013.01); *A61L 2430/22* (2013.01); *C12N 2501/056* (2013.01); *D10B 2331/00* (2013.01); *D10B 2401/12* (2013.01); *D10B 2509/00* (2013.01)

(58) Field of Classification Search
CPC ... C12N 5/0668; A61L 27/3691; A61L 27/26; A61L 27/54
See application file for complete search history.

(56) References Cited

U.S. PATENT DOCUMENTS

| | | |
|---|---|---|
| 8,574,567 B2 | 11/2013 | Crawford |
| 9,345,486 B2 | 5/2016 | Zhang |
| 2014/0017787 A1 | 1/2014 | Betancourt |
| 2014/0023723 A1 | 1/2014 | Leach |
| 2015/0086607 A1 | 3/2015 | Johnson |

OTHER PUBLICATIONS

Waterman, R., et al., A New Mesenchymal Stem Cell (MSC) Paradigm: Polarization into a Pro-Inflammatory MSC1 or an Immunosuppressive . . . , PLOS1, 2010, p. e10088, vol. 5(4).
Young, Lee W., International Search Report, PCT Application PCT/US2016/055035, dated Feb. 17, 2017, ISA/US, Alexandria, VA.
Young, Lee W., Written Opinion of the International Searching Authority, PCT Application PCT/US2016/055035, dated Feb. 17, 2017, ISA/US, Alexandria, VA.

*Primary Examiner* — Teresa E Knight
(74) *Attorney, Agent, or Firm* — Laurence J. Hyman; Hyman IP Law

(57) ABSTRACT

The invention provides devices for supporting regeneration of body tissue and of tubular structures, such as the esophagus or intestine, and methods for making and for using the devices.

36 Claims, 3 Drawing Sheets

DEVICES FOR SUPPORTING REGENERATION OF BODY TISSUES, AND METHODS OF MAKING AND USING THEM

CROSS-REFERENCE TO RELATED APPLICATIONS

This application claims the benefit and priority of U.S. Provisional Patent Application No. 62/234,744, filed Sep. 30, 2015, the contents of which are hereby incorporated by reference in their entirety.

STATEMENT OF FEDERAL FUNDING

The invention was made with U.S. Government support under NSF-IGERT Fellowship No. 1144646, awarded by the National Science Foundation. The government has certain rights in the invention.

BACKGROUND OF THE INVENTION

Current techniques for repairing damage to bodily organs and structures due to disease, congenital defects, or traumatic injury, are often unsatisfactory. For example, the current standard treatment for replacing portions of an esophagus damaged by disease or traumatic injury is an operation called a "gastric pull-up," in which the damaged portion of the esophagus is removed and the stomach or even the large intestine is sutured to the remaining undamaged esophageal tissue. For esophageal cancer patients, an esophagectomy is performed in which the cancerous tissue is surgically removed and the resected tissue of the esophagus is reconstructed from the stomach or large intestine. These procedures result in a low quality of life for the patient, who have to receive nutrition through a feeding tube. Further, these procedures have unattractive clinical outcomes: after an esophagectomy the surgical complication rates are 40-80%, the morbidity rates are 50-60%, the mortality rates 30 days after the procedure are about 22%, and the 5-year survival rate is less than 20%.

While the clinical results are not outstanding, the costs of these repair procedures can be prohibitive. Using the esophagus as an example, an esophagectomy procedure typically costs $110,000 and requires 5 years of follow-up medical expenses totaling some $23,000-$60,000. The length of time needed for recovery from an esophagectomy under the current standard of care compounds the cost burden on patients.

It would be desirable to have an implantable medical device that can be used to replace some or all of a damaged or diseased esophagus. It would also be desirable to have such devices to support regeneration of other damaged tissues and bodily organs, particularly tubular organs. Surprisingly, the present invention satisfies these and other needs.

PARTIES TO JOINT RESEARCH AGREEMENT

Not applicable.

REFERENCE TO SEQUENCE LISTING OR TABLE SUBMITTED ON COMPACT DISC AND INCORPORATION-BY-REFERENCE OF THE MATERIAL

Not applicable.

BRIEF SUMMARY OF THE INVENTION

In some embodiments, the invention provides implantable medical devices for use in a mammal, comprising (a) a scaffold comprising a meshwork of nanofibers of resorbable, non-toxic polymer and chitosan, and (b) factors on the scaffold from isolated mesenchymal stem cells (MSCs) primed along an anti-inflammatory pathway. In some embodiments, the resorbable, non-toxic polymer is poly (caprolactone) ("PCL"), polyglycolide ("PGA"), poly(lactide-co-glycolide) ("PLGA"), polylactide-co-caprolactone ("PLCL"), polydioxanone ("PDO"), poly(3-hydroxybutyrate-co-3-hydroxyvalerate) ("PHBV"), poly(β-hydroxybutyrate) ("PHB"), polyanhydrides, poly trimethyl carbonate, poly (glycolide-co-trimethylene carbonate), (poly (lactic-co-glycolic acid), poly(glycolide-co-caprolactone), poly(DTH iminocarbonate), poly(bisphenol A iminocarbonate), polyurethane, polycyanoacrylate, and polyphosphazenepolycaprolactone, polylactic acid ("PLA"), or collagen. In some embodiments, the resorbable, non-toxic polymer is PCL, PGA, PLA, PLGA, polydioxanone, trimethylene carbonate, or polyanhydride. In some embodiments, the resorbable, non-toxic polymer is PCL. In some embodiments, the MSCs have been primed along an anti-inflammatory pathway by incubating said isolated MSCs cells with a Toll-like receptor ("TLR") 3 agonist. In some embodiments, the TLR 3 agonist is IL4, IL13, polyadenosine:polyuracil (poly(A:U)), polyinosinic:polycytidylic acid (poly(I:C)), rintatolimid, RGC100, a derivative of poly(I:C) that is an agonist of TLR3, and poly(C:G/I). In some embodiments, the TLR3 agonist is poly(I:C). In some embodiments, the nanofibers are electrospun. In some embodiments, the isolated MSCs are allogeneic. In some embodiments, the isolated MSCs are adipose-derived MSCs or bone-marrow-derived MSCs. In some embodiments, the mammal is a human and said isolated MSCs are allogeneic human MSCs.

In another group of embodiments, the invention provides methods for making an implantable medical device of a desired shape for use in a mammal. The methods comprise the following steps, performed in the following order: (a) providing a scaffold of a nanofiber meshwork in said desired shape, the nanofiber meshwork comprising nanofibers of a resorbable, non-toxic polymer and chitosan, (b) seeding the scaffold with isolated mesenchymal stem cells (MSCs), (c) incubating the isolated MSCs on the scaffold, and (d) decellularizing the scaffold of the isolated MSCs, thereby making the implantable medical device in the desired shape. In some embodiments, the decellularizing comprises freeze-thawing of the scaffold seeded with the isolated MSCs. In some embodiments, the method further comprises step (e), lyophilizing said scaffold following said decellularization. In some embodiments, the incubation of step (c) is for about 24 hours to about 240 hours. In some embodiments, the incubation of step (c) is for about 24 hours to about 96 hours. In some embodiments, the MSCs are primed along an anti-inflammatory pathway prior to or during step (b) or step (c). In some embodiments, the MSCs are primed along an anti-inflammatory pathway by incubating the isolated MSCs with a Toll-like receptor ("TLR") 3 agonist. In some embodiments, the incubation with the TLR3 agonist is for about 10 minutes to about 2 hours. In some embodiments, the TLR 3 agonist is IL4, IL13, polyadenosine:polyuracil (poly(A:U)), polyinosinic:polycytidylic acid (poly(I:C)), rintatolimid, RGC100, a derivative of poly(I:C) that is an agonist of TLR3, and poly(C:G/I). In some embodiments, the TLR3 ligand is poly(I:C). In some embodiments, the nanofibers are electrospun. In some embodiments, the isolated MSCs are allogeneic. In some embodiments, the isolated MSCs are adipose-derived MSCs or bone-marrow-derived MSCs. In some embodiments, the mammal is a human and the isolated MSCs are allogeneic human MSCs.

In another group of embodiments, the invention provides compositions for making an implantable medical device for use in a mammal, comprising (a) a scaffold comprising a meshwork of nanofibers of resorbable, non-toxic polymer and chitosan, and (b) isolated mesenchymal stem cells (MSCs) primed along an anti-inflammatory pathway. In some embodiments, the resorbable, non-toxic polymer is poly(caprolactone) ("PCL"), polyglycolide ("PGA"), poly(lactide-co-glycolide) ("PLGA"), polylactide-co-caprolactone ("PLCL"), polydioxanone ("PDO"), poly(3-hydroxybutyrate-co-3-hydroxyvalerate) ("PHBV"), poly(β-hydroxybutyrate) ("PHB"), polyanhydrides, poly trimethyl carbonate, poly (glycolide-co-trimethylene carbonate), (poly(lactic-co-glycolic acid), poly(glycolide-co-caprolactone), poly(DTH iminocarbonate), poly(bisphenol A iminocarbonate), polycyanoacrylate, and polyphosphazenepolycaprolactone, polylactic acid ("PLA"), gelatin, polyurethane, or collagen. In some embodiments, the resorbable, non-toxic polymer is PCL. In some embodiments, the MSCs are primed along an anti-inflammatory pathway by incubating said isolated MSCs cells with a Toll-like receptor ("TLR") 3 agonist. In some embodiments, the TLR 3 agonist is IL4, IL13, polyadenosine:polyuracil (poly(A:U), polyinosinic:polycytidylic acid (poly(I:C)), rintatolimid, RGC100, a double stranded RNA that is an agonist of TLR3, a derivative of poly(I:C) that is an agonist of TLR3, or poly(C:G/I). In some embodiments, the TLR3 ligand is poly(I:C). In some embodiments, the nanofibers are electrospun. In some embodiments, the isolated MSCs are allogeneic. In some embodiments, the isolated MSCs are adipose-derived MSCs or bone-marrow-derived MSCs. In some embodiments, the mammal is a human and the isolated MSCs are allogeneic human MSCs.

In another group of embodiments, the invention provides methods of treating a mammal in need thereof with an implantable medical device of a desired shape and size, comprising implanting into said mammal a nanofiber meshwork scaffold in the desired shape and size, the scaffold consisting of (a) nanofibers of a resorbable, non-toxic polymer and chitosan, and (b) factors from isolated mesenchymal stem cells (MSCs) which have been primed along an anti-inflammatory pathway, thereby treating said mammal with said implantable medical device.

DETAILED DESCRIPTION

A. Introduction

Figure 1:
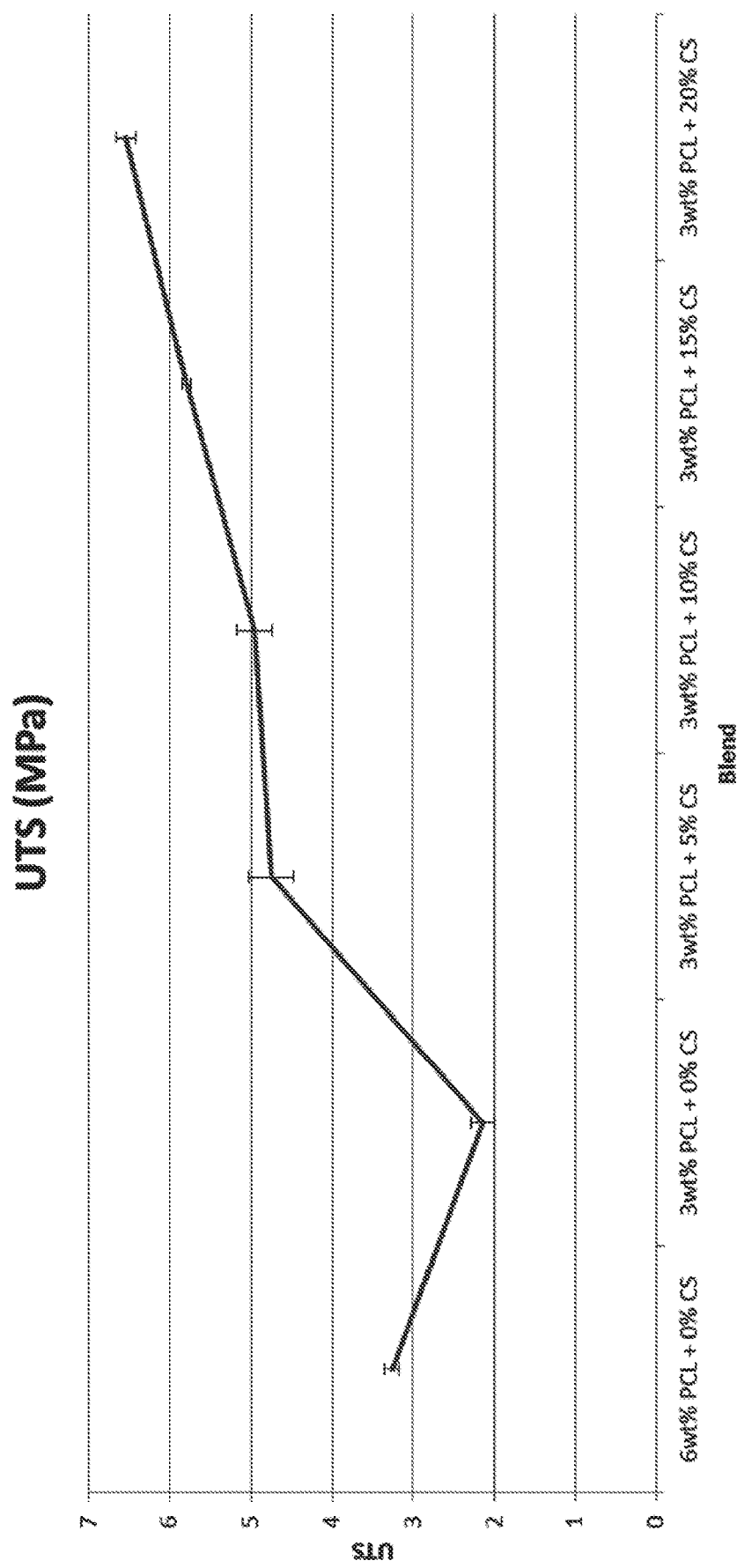
FIG. 1 is a graph showing the ultimate tensile strength ("UTS") in megaPascals (MPa) of tensile coupons of different concentrations of poly(caprolactone) ("PCL") by itself and of PCL blended with different concentrations of chitosan ("CS"). As can be seen in FIG. 1, the ultimate tensile strength of the PCL/CS blend increased as the percentage of chitosan in the blend increased. The graph shows the average value of five replicates for each composition.

Efforts have been made for some time to engineer replacements for some or all of an esophagus damaged by disease or injury. Replacements have included starting with a patient's own decellularized tissue, or using nanofiber meshwork scaffolds on which a variety of cell types or cell-derived factors have been seeded. Unfortunately, attempts to provide engineered replacement esophagi or supports on which esophagi can regenerate have been not provided satisfactory solutions. Some have tended to provoke scarring or other fibrotic or inflammatory responses that have resulted in significant constriction of the lumen of the organ. Other approaches have shown regeneration of all layers of the esophagus, but have required frequent application of patient plasma or procedures first to place and then to remove the devices.

Surprisingly, the inventive devices, methods, and compositions, provide an off-the-shelf solution that provides a support on which portions of damaged body tissues can regenerate. The support can be, for example, a flat or shaped sheet that can serve as a patch for an area of damaged tissue or can be a tubular scaffold to replace a portion of a tubular organ or portion of an organ, such as an esophagus, an intestine, or a blood vessel. The inventive devices and methods of making and using them provide an artificial nanofiber meshwork scaffold of resorbable, non-toxic materials, with interstitial spaces which can be populated by progenitor cells of the organ once the scaffold is implanted. Further, the inventive devices have disposed on their surface one or more extracellular matrix ("ECM") factors that promote recruitment of organ progenitor cells and one or more anti-inflammatory factors that reduce inflammatory or fibrotic responses by surrounding tissue that would potentially compromise the device's utility.

In studies underlying the present disclosure, tubular scaffolds of some embodiments of the invention were implanted in a murine model adjacent to the intestine. To avoid the need to perform microsurgery on the animals, in these studies, the scaffolds were wrapped in omentum, a fold of peritoneum in the abdominal cavity, and placed adjacent to the intestine but not in immediate contact with it. The animals did not show evidence of inflammatory responses when observed over a 30 day period following implantation. The animals were then sacrificed and the skin around the implant shaved and visualized. No redness or swelling was observed around the area of the implant. The scaffolds were then removed from the animals and H&E staining was performed to observe the morphology, nuclei and cytosol of any cells in the scaffold. A robust population of gastrointestinal cells was seen in the scaffold, but few, if any, lymphocytes, indicating there was recruitment of gastrointestinal cells, but little if any inflammatory response. In clinical use, a tubular scaffold would typically be joined to the organ being repaired by surgical anastomosis and a flat or shaped patch would be sutured in place by a laparoscopic procedure or in the case of an esophagus, held in placed by an esophageal stent, without a tissue such as the omentum being placed between the implanted device and the organ being repaired.

The resorbable, non-toxic materials of the devices are expected to degrade over a period of months, and the degradation products to be excreted or utilized by the body, while the progenitor cells that have been recruited into and populated the device will result in forming layers of cells that will remain in place and serve as a replacement for the portion of the tubular organ in which the device was implanted. It is noted that scaffolds by others, made of different materials or using different culture techniques, have reported that keratinized epithelial cells were recruited into and lined their esophageal implants within a few days, and eventually developed all four layers of the esophageal tissue. Based on those results, we expect to see similar development of some and even all of the layers of the esophagus, and some or even all of the cells layers of the intestine.

In some embodiments, the inventive methods relate to providing scaffolds of a meshwork of nanofibers of one or more of the synthetic resorbable, biocompatible polymers discussed in Section B, below, and chitosan, discussed in Section C, below. The scaffolds are then seeded with allogeneic mesenchymal stem cells (sometimes abbreviated herein as "MSCs"), and allowed to incubate for a period of time. The use of allogeneic MSCs in the inventive methods and devices is an advantage over other approaches, as it allows the devices to be prepared in advance of need and ready for implantation without having a substantial delay to wait while a patient's MSCs are harvested and incubated on a device before the device can be implanted in the patient. In preferred embodiments, the MSCs have been primed or polarized along an anti-inflammatory pathway, and in preferred embodiments, have been primed along this pathway by being contacted with an agonist of Toll-like receptor 3 (as discussed below, MSCs primed in this manner are sometimes referred to herein as MSC2s). The scaffolds are then subjected to decellularization to remove the MSCs, and stored until needed. Preferably, the decellularization is by subjecting the scaffolds to repeated freeze-thaw cycles. Freeze-thaw decellularization avoids the residual surfactant contaminants that can be left over from traditional decellularization protocols. Removal of the MSCs by decellularization provides another advantage of the inventive devices by eliminating the potential for development of an immune response to the allogeneic cells over time.

Surprisingly, immunohistochemical studies showed that the decellularized scaffolds retain at least one important extracellular matrix ("ECM") protein and one anti-inflammatory factor that have been secreted from the MSCs during the incubation period, released during the decellularization process, or both, and it is believed that additional factors for which immunohistochemistry studies have not yet been performed are likely to be present. It is believed that the presence of these factors on the scaffold is advantageous and provides a surprising advantage of the inventive devices compared to scaffolds made from other methods, including those made with the same polymer compositions, but without the incubation of primed MSC2s on the scaffold and subsequent decellularization. While MSCs are generally believed to be safe and are implantable without provoking a harmful immune response, removing the MSCs from the scaffolds before implantation ensures that the scaffold is populated only by endogenous cells.

As noted, the inventive devices comprise chitosan as well as at least one synthetic polymer. Cells can adhere to chitosan, and it is believed that this property facilitates adhesion of MSCs to the scaffolds during the incubation noted above. Importantly, however, chitosan itself not only has anti-inflammatory properties but it also promotes differentiation of myoblasts into myocytes. It is believed that the combination of (a) the anti-inflammatory property of chitosan in the scaffolds, (b) the ability of chitosan in the scaffold to activate progenitor cells in tissue surrounding the device following implantation, and (c) the presence of anti-inflammatory factors and ECM protein or proteins on the scaffolds following decellularization of the MSCs, better supports and induces regeneration of tissues or organs then do previously available devices. The combination of these factors may indeed provide surprisingly better results than would be expected based on results by the use of chitosan or by the use of MSC2s on scaffolds without decellularization of the scaffolds.

The inventive devices thus provide an off-the-shelf solution for repairing tissues. In some embodiments, the inventive devices can be formed as a patch to provide a regenerative support to repair a hole in an organ such as an esophagus. In these embodiments, the device is typically shaped to be flat or to have a curved contour matching as closely as possible that of the area of intended use. In other embodiments, the devices allow replacing portions of the esophagus or other tubular tissues or organs, such as the small intestine. Scaffolds can be designed in a variety of shapes, including sheets or tubes, and of various lengths, widths, and thicknesses, allowing the practitioner, such as a surgeon, or in the case of the esophagus, a thoracic surgeon or cardiothoracic surgeon, to select a scaffold with a shape, length, width, and thickness suitable for the intended use in the patient. As the inventive devices do not have a sphincter, devices intended to replace portions of the esophagus are desirably implanted between the upper and the lower esophageal sphincters. It is anticipated that the experienced surgeons who perform the current art-standard gastric pull-up operation to replace a damaged esophagus, in which some of the damaged esophagus is removed and the stomach or (if necessary) the intestine is extended to whatever portion remains, are familiar with the tradeoffs required to balance the need to remove some or all of a patient's organ and the benefits and limitations of any particular therapeutic option. It is anticipated that the inventive devices will be able to replace up to approximately two-thirds of a patient's esophagus, preferably not including the upper or lower sphincters. It is anticipated that the devices will be connected appropriately at both ends by surgical anastomosis.

As persons of skill will appreciate, the esophagus is composed of multiple layers of tissue. Some diseases, such as gastroesophageal reflux disease ("GERD"), may have damaged some but not all of the layers. In some embodiments, the scaffold can be sized to the length of the damaged section and to the thickness of the layers that have been damaged and used to support the undamaged portion of the esophagus while supporting repair of the damaged layers. In other diseases, such as a cancer that has not penetrated all of the layers of tissue, the practitioner may determine that the patient will have a better post-operative quality if the cancerous tissue is ablated, without removal of the portion of the esophagus in which the cancerous tissue resides. In such cases, the practitioner can ablate the cancerous tissue by standard methods, such as by endoscopically burning off the cancerous tissue, and then implant one of the inventive devices, sized to extend along the area treated, and of a thickness replacing that of the layer(s) of tissue lost to the procedure, to line the treated area. Conveniently, devices used to line a portion of damaged esophagus may be put in place by endoscopic means. Procedures to replace a portion of a damaged or diseased esophagus or intestine may be done by conventional open surgery. Alternatively, where the esophagus has developed a hole or an eroded area, perhaps due to GERD or to trauma, a flat or curved device can be put in place and either sutured in place laparoscopically or held in place by an esophageal stent.

B. Resorbable, Non-Toxic Polymers

Resorbable, non-toxic polymers are preferred for combination with chitosan in the inventive devices and methods. For example, polylactide ("PLA"), a biodegradable polymer, has been used in a number of medical device applications. A number of synthetic biodegradable polymers are known and are approved or under investigation for biomedical use, including, for example, polyglycolide ("PGA"), poly(lactide-co-glycolide) ("PLGA"), poly(caprolactone) ("PCL"), polylactide-co-caprolactone ("PLCL"), polydioxanone ("PDO"), poly(3-hydroxybutyrate-co-3-hydroxyvalerate) ("PHBV"), poly(β-hydroxybutyrate) ("PHB"), polyanhydrides, poly trimethyl carbonate, poly (glycolide-co-trimethylene carbonate), (poly(lactic-co-glycolic acid), poly(glycolide-co-caprolactone), poly(DTH iminocarbonate), poly(bisphenol A iminocarbonate), polycyanoacrylate, polyphosphazene, and polyurethane ("PU"). The compounds most widely used in commercial applications include PGA and PLA, followed by PLGA, PCL, polydioxanone, trimethylene carbonate, and polyanhydride. In some preferred embodiments, the resorbable, non-toxic polymer is PCL. As used herein, "resorbable" means a polymer that can be degraded in situ in the body of a subject in which it is implanted, and metabolized or excreted. As used herein, "non-toxic" means that neither the polymer nor its degradation products are toxic or will cause chronic inflammation or an immune response in the subject in which the polymer has been implanted, given the amount of the polymer to be implanted and the amount of the degradation product(s) that will result from degradation of the amount of the polymer to be implanted.

Any particular resorbable polymer can be used so long as neither it nor its degradation products are toxic, it can form a polymer with chitosan that has acceptable biomechanical properties (e.g., sufficient elasticity and resistance to tearing) and adherence of anti-inflammatory factors when seeded with and incubated with primed mesenchymal stem cells, and it resorbs when implanted in a subject's body over a period of a month to one year, with a resorption period of three to nine months being preferred. The use of resorbable materials rather than an implant that remains intact in the body is preferred as resorption of the device eliminates the possibility the device will provoke a chronic inflammatory or immune response. As explained in Section C, below, for convenience of reference herein, the phrases "resorbable, non-toxic polymer" and "resorbable, biocompatible polymer," and the term "polymer" as used herein refer to a synthetic polymer, such as the ones described in the preceding paragraph, while the term "chitosan" denotes the natural polymer known by that name, discussed in the next section.

C. Chitosan

Chitosan is described by Wikipedia as a linear polysaccharide composed of randomly distributed β-(1-4)-linked D-glucosamine (deacetylated unit) and N-acetyl-D-glucosamine (acetylated unit). It is typically prepared by deacetylating chitin. Chitosan is commercially available from, for example, Sigma-Aldrich Co. (St. Louis, Mo.), which sells chitosan in a variety of molecular weight ranges. All molecular weights of chitosan can be used in making the inventive devices, and all deacetylated values are suitable, with chitosan that has been deacytelated to higher percentages being preferred over chitosan that has been deacetylated to a lower percentage.

The inventive methods and devices relate to combinations of one or more of the resorbable, non-toxic polymers discussed in the previous section and chitosan. Without wishing to be bound by theory, it is believe that the presence of chitosan facilitates adherence of mesenchymal stem cells to the scaffold and may contribute to adherence of anti-inflammatory factors or other beneficial factors secreted by the MSCs during incubation or released from the MSCs during decellularization.

While chitosan is itself a non-toxic polymer, for ease of reference, the phrase "resorbable, non-toxic polymer" or the word "polymer" by itself as used herein refers to a synthetic polymer, such as those described in Section B, above but does not include chitosan, which is instead specifically referenced by its name whenever its presence is intended.

D. Methods of Preparing Scaffolds of Nanofiber Meshwork

The scaffolds can be prepared by any conventional technique capable of providing a nanofiber meshwork of the resorbable, non-toxic polymer(s) and chitosan of the desired shape, size and thickness. For example, the scaffolds can be prepared by extruding nanofibers of the polymers and shaping them around a mandrel or other form in the desired shape and layered in a random mesh pattern until the desired thickness (for example, the thickness of the mucosa and lamina propria layers of the esophagus) is reached.

In some preferred embodiments, the scaffolds are prepared by electrospinning. It is expected that persons of skill are familiar with electrospinning, but, briefly, a spinneret, such as a hypodermic needle, is connected to a high power direct current supply, a syringe pump, and a polymer solution. Across a gap is a grounded collector, such as a mandrel, in the desired shape and size of the object to be electrospun. The collector is typically rotated. An electric charge differential is created between the spinneret and the collector and the polymer solution is extruded from the needle tip. The solvent in the polymer typically evaporates as the polymer crosses the gap, resulting in a nanofiber of the polymer. As the collector rotates, the nanofiber is typically disposed over the collector in an irregular pattern. As layers of the nanofibers accumulate on the collector to the desired thickness, the irregular pattern of the nanofibers results in the formation of a nanofiber meshwork in the shape of the underlying collector. In some embodiments, the mandrel is smooth. In some embodiments, the mandrel can have small peaks and valleys to augment the three-dimensionality of the meshwork into which MSCs will be seeded and, later, into which cells of the subject can migrate when the device is implanted, but which are small enough so the peaks and valleys do not interfere with sliding the scaffold off the mandrel. The scaffolds are typically slid off the mandrel once the scaffold has reached the desired thickness.

As used herein, the term "comprising" with respect to the scaffolds means a composition contains the recited materials but can also include other, unrecited materials, while the phrase "consisting essentially of" means a composition that contains the recited materials and unrecited materials that do not materially affect the basic and novel characteristics of the inventive devices. The term "consisting of" is used to refer to compositions that exclude any material not specified. It is specifically noted that, in applying the terms to the inventive scaffolds, they are used to refer to the materials of which the nanofibers of the meshwork are made. As discussed further below, the anti-inflammatory factors and pro-regenerative factors which are deposited on the nanofibers by MSCs during the incubation or decellularization process, or both have not been fully elucidated and these factor not are intended to be excluded by the terms "comprising," "consisting essentially of," or "consisting of." In some embodiments, the nanofibers of the scaffolds comprise one or more of the synthetic polymers discussed above, and chitosan. In some embodiments, the nanofibers of the scaffolds consist essentially of one or more of the synthetic polymers discussed above, and chitosan. In some embodiments, the nanofibers of the scaffolds consist of one or more of the synthetic polymers discussed above, and chitosan. In some embodiments, the nanofibers of the scaffolds consist of PCL and chitosan. In some embodiments, the nanofibers of the scaffolds consist of about 3 wt % of PCL and about 4% to about 13% chitosan, where the term "about" means ±½ percent and the percentage of chitosan stated is of the dry weight of PCL present in the composition.

E. Dissolving Polymer Solutions

The nanofiber meshwork of the resorbable, non-toxic polymer(s) and chitosan are typically made by dissolving the polymers into a solution and then forming the nanofiber meshwork by means, such as electrospinning, described in the preceding section. The resorbable, non-toxic polymer(s) can be in one solution and the chitosan in a second. Where electrospinning is used, for example, two spinnerets can be used to allow nanofibers from both solutions to be applied to the collector simultaneously. In preferred embodiments, the resorbable, non-toxic polymer(s) and the chitosan are dissolved in a single solution.

Typically, the resorbable, non-toxic polymer(s) is dissolved using an acid, such as glacial acetic acid or acetic acid in water, as the solvent. The addition of even small amounts of chitosan causes the viscosity of the solution to increase substantially. Use of a solvent with a high vapor pressure, such as hexafluoro isopropanol ("HFIP") with an acid solvent is desirable to increase the volatility of the solution for electrospinning. In studies underlying the present disclosure, the solution used to dissolve the resorbable, non-toxic polymer(s) and chitosan was 95% HFIP and 5% glacial acetic acid. It is expected that other solvent combinations will allow electrospinning nanofibers from solutions of resorbable, non-toxic polymer(s) and chitosan.

F. Making Nanofibers with Desired Physical Properties

To be suitable for use as an implantable device to replace a portion of an esophagus, the device preferably has elasticity and sufficient tensile strength not to tear as food traverses through the esophagus or as the subject bends or twists. More elasticity, or the ability to elongate, is preferable over less elasticity.

A series of studies were performed to determine the physical properties of particular combinations of an exemplar resorbable, non-toxic polymer, PCL, and chitosan. Mixtures of different percentages of PCL and chitosan were made and subjected to standard tests for universal tensile strength, elongation, and modulus. Such measurements are standard in the art and are typically performed on so-called universal testing machines, or "UTMs". UTMs are commercially available from, for example, Admet, Inc. (Norwood, Mass.), TestResources, Inc. (Shakopee, Minn.), Thwing-Albert Instrument Co. (West Berlin, N.J.), and Instron (Norwood, Mass.).

Figure 2:
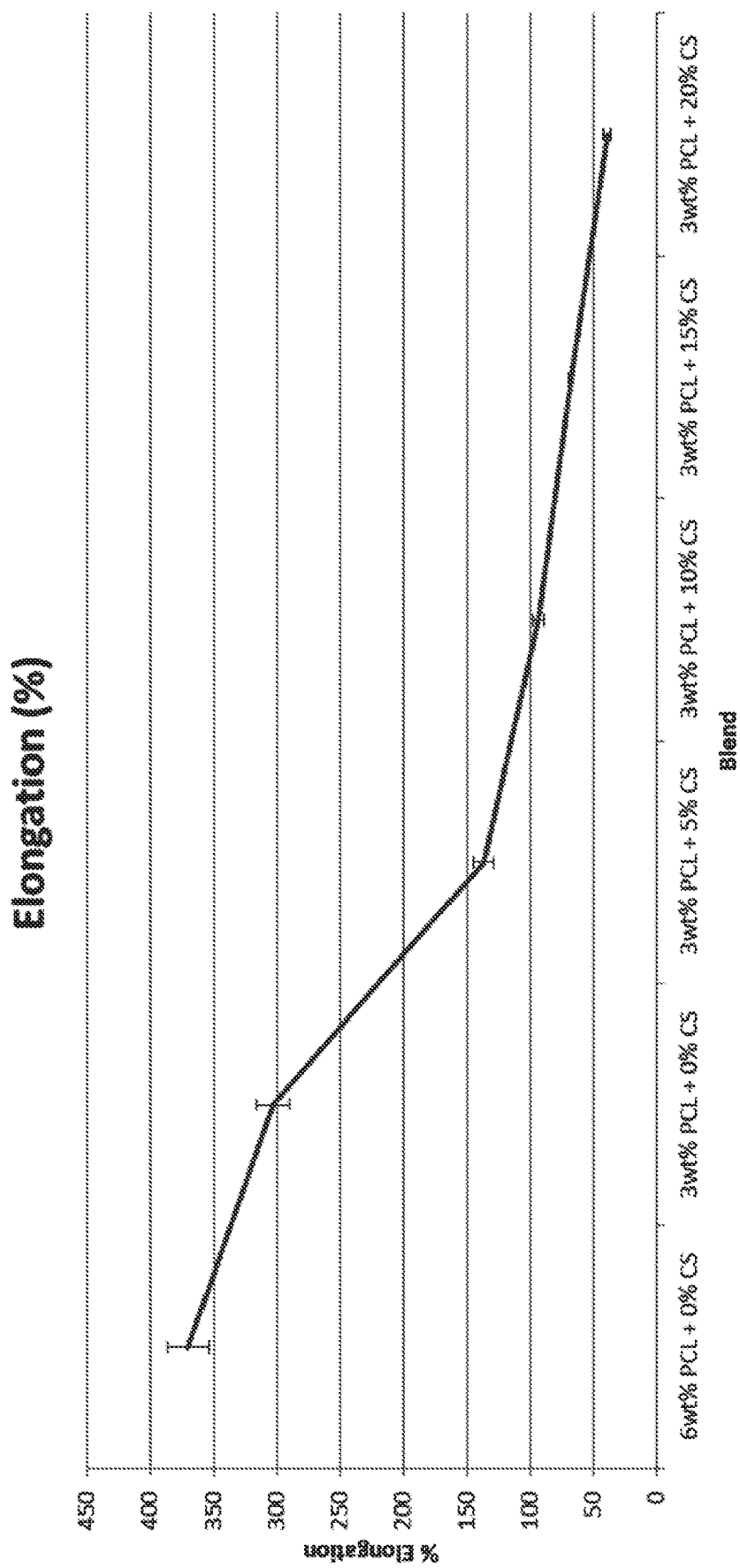
FIG. 2 is a graph showing how much tensile coupons of poly(caprolactone) ("PCL") or of PCL blended with different concentrations of chitosan ("CS") could elongate from their initial length before failing. The percentages decrease substantially as chitosan is introduced at 5%, and to continue to decrease as the percentage of chitosan in the blend increases. Elongation is measured as the extent to which the material could be stretched from its initial size before failure. A measurement of 100% elongation, for example, would indicate that the material was able to double in length from its initial length before failure. The graph shows the average value of five replicates for each composition.
Figure 3:
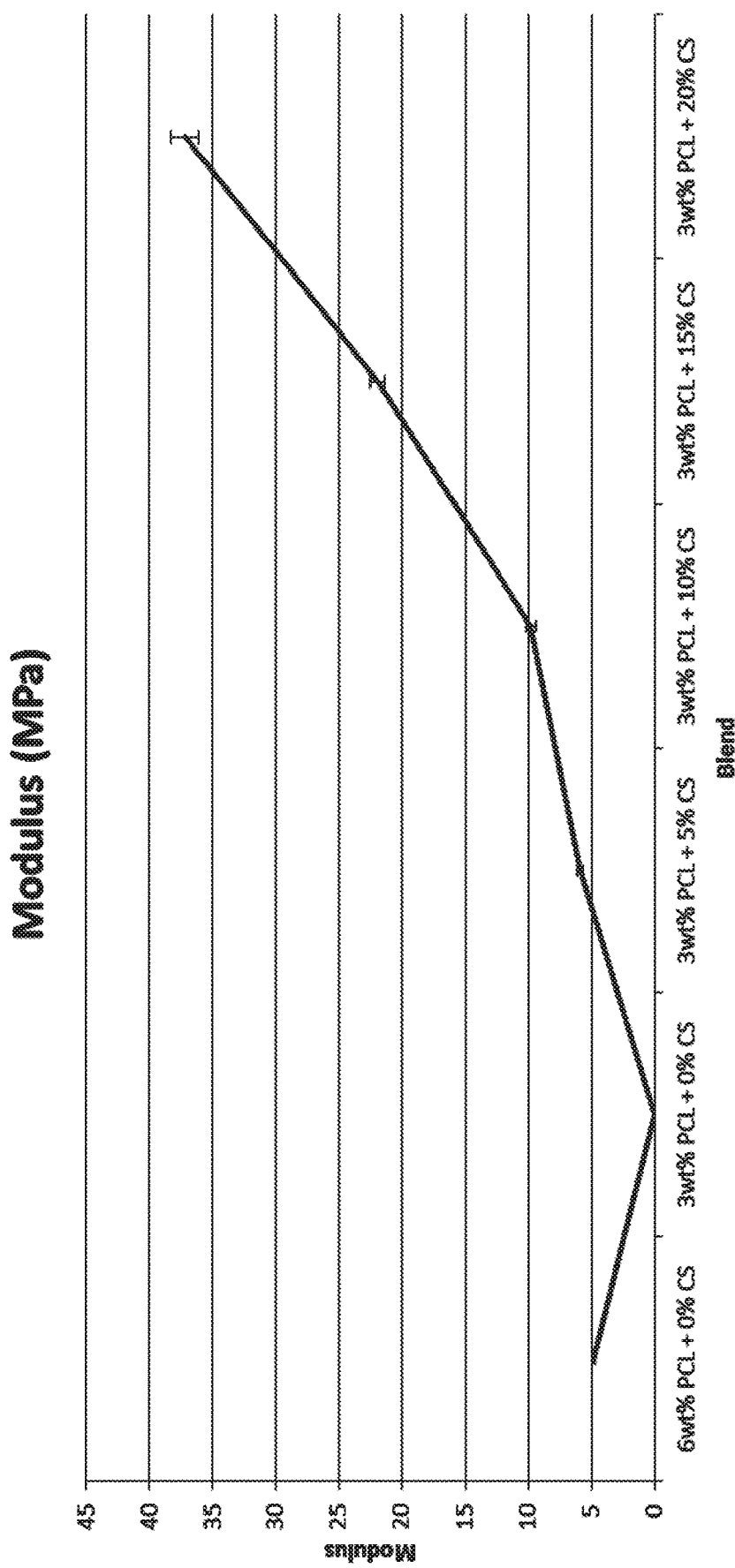
FIG. 3 is a graph showing the modulus of elasticity in megaPascals of tensile coupons of poly(caprolactone) ("PCL") or of PCL blended with different concentrations of chitosan ("CS") the material. The modulus increases notably as the percentage of chitosan in the blend increases. The graph shows the average value of five replicates for each composition.

The results of the studies are reported in the Examples, but in brief, there was an inverse relationship between the tensile strength of the combination, which went up as the percentage of chitosan relative to PCL increased, and the elasticity of the combination, which dropped as the percentage of chitosan increased. More elasticity is more desirable than less elasticity, and in mixtures in which the chitosan was greater than about 15% of the solid weight of the PCL component, the elasticity was below a point deemed acceptable. The results of the studies are shown in FIGS. 1-3. In the studies whose results are reported in these Figures, the chitosan percentage is stated as a percentage of the dry weight of the PCL used in each "blend". To provide a hypothetical example, if 3 grams of PCL was dissolved in 97 grams of 95% HFIP/5% glacial acetic acid, a 5% solution of chitosan would be made by adding 5% of 3 grams, or 0.15 grams of chitosan, to the solution.

Of the three Figures, FIG. 3, which presents the elastic, or Young's, modulus, measures a combination of the tensile strength and elongation of the tested material, by a formula of stress over strain, and provides information on how much stress and strain the material can undergo before it fails. The results depicted in FIG. 3 show that, at 20% chitosan, the modulus is over 35, which indicates it would not have sufficient resistance to strain and would tear in use. The PCL/chitosan blend with 15% chitosan relative to the dry weight of the PCL prior to being dissolved into the solvent had a modulus of just over 20, which is considered to be at or above the maximum modulus acceptable for use in this application, and also had an elongation measured at approximately 60%, which is marginal for this application, in which one wishes to maximize elongation to the maximum consistent with tearing resistance. A blend with 5% chitosan showed a modulus of just over 5, indicating that the percentage of chitosan could be decreased by yet a percent or two and still result in a blend with satisfactory characteristics. In preferred embodiments, the modulus of elasticity for polymer/chitosan blends should be between about 3 to about 15, more preferably 4 to about 14, and more preferably about 4 to about 13, 4 to about 12, and 4 to about 11. In some embodiments, the modulus of elasticity is preferably about 5 to about 10. In general, when blended with PCL, 10% chitosan provided the best balance of elongation and modulus. Accordingly, for use in devices intended to replace or support the esophagus or intestine, PCL should be blended with 3%-14% chitosan, preferably about 4% to about 13% chitosan, more preferably about 4% to about 11% chitosan, even more preferably about 5% to about 11% chitosan, yet more preferably about 6% to about 11% chitosan, preferably about 6, 7, 8, 9 or 10% chitosan. As used in this paragraph, "about" means ±0.5% of the stated value.

While these studies employed blends made with PCL as an exemplar of a resorbable, biocompatible polymer to be used in combination with chitosan, persons of skill can readily determine percentages of chitosan to be used in combination with any of the other resorbable, biocompatible polymers set forth in Section B, that will result in a combination having an elastic modulus and elongation with values in the range indicated above as being satisfactory. The modulus and elasticity of any particular tissue, or of an organ of interest, such as the esophagus or the intestine, can be readily determined and a polymer/chitosan blend selected that has a modulus of elasticity identical to or within a few percent of that of the tissue or organ of the species of interest. Preferably, the modulus of elasticity of the polymer/chitosan blend is within 33% of the modulus of elasticity of the tissue or organ of interest, more preferably within 25% of the modulus of elasticity, still more preferably within 20%, 15%, 10, 9%, 8%, 7%, 6%, 5%, 4%, 3%, 2% or 1% of the modulus of elasticity of the tissue or organ of interest. While most of the inventive devices will be intended for use in humans, veterinary uses are also contemplated, and the modulus of elasticity of a tissue or organ of interest, such as an esophagus, of a mammalian species of interest, such as a horse, dog, or cat can likewise be readily determined. Testing the modulus of elasticity of various materials is well known in the art but, briefly, the tissue or organ of interest would generally be surgically removed from a fresh cadaver of the species of interest, fashioned into a "tensile coupon," and the modulus of elasticity of the tensile coupon would be determine using a so-called universal testing machine, as described elsewhere herein. If the modulus of elasticity for the organ of interest in the species of interest differs substantially from that of humans, a polymer/chitosan blend that matches or is close to the modulus of elasticity for the organ of interest in the non-human mammalian species of interest can be designed and used to make one of the inventive devices of the invention made for use in an animal of the species of interest. Preferably, the MSCs incubated on the scaffold are allogeneic MSCs of the species of interest.

G. Mesenchymal Stem Cells and Priming them Along an Anti-Inflammatory Pathway

Mesenchymal stem cells (sometimes now referred to as "mesenchymal stromal cells"), abbreviated herein as "MSCs," are multipotent, bone-derived cells that can differentiate into a variety of cell types. They are readily separated from other bone-derived cells by their adherence to plastic. Human MSCs are commercially available from several sources, including Lonza Inc. (Allendale, N.J.), and Sigma-Aldrich Co., LLC (St. Louis, Mo.). Lonza, for example, sells "Poietics™ Normal Human Bone Marrow Derived Mesenchymal Stem Cells." Sigma-Aldrich and Lonza also sell media for proliferating MSCs in an undifferentiated state, and Lonza sells media for differentiating MSCs along any of three different pathways, and provides storage and use protocols for each medium.

In 2010, Waterman et al. reported that agonists of Toll-like receptor 3 ("TLR3") polarized MSCs toward an immunosuppressive phenotype, which they termed "MSC2". Waterman, et al., PLoS ONE 5(4): e10088. doi:10.1371/journal.pone.0010088 (2010) ("Waterman 2010," incorporated herein by reference). In U.S. Published Patent Application 2014/0017787 (hereafter, the "'787 publication"), Betancourt reported a number of TLR3 agonists: IL4, IL13, poly(adenosine:uracil) (abbreviated as "poly(A:C)"), or poly(inosinic:polycytidylic acid) (abbreviated as "poly(I:C)"), or combinations thereof, and that they could be delivered by incubation, transfection, transduction, by carrier molecules, or by combinations thereof. (The '787 publication is hereby incorporated by reference.) The '787 publication states that, preferably, the TLR3 agonist is poly(I:C). It further reports that the hMSCs studied were grown to 60-70% confluency in growth medium (DMEM-alpha and 16.5% fetal calf serum (FCS)) prior to contact with a TLR3 agonist. TLR3-agonists were then added to fresh growth medium and incubated with the cells for 1 hr. Then, the cells were washed twice in growth medium without the TLR3 agonists and assayed. It further states that the TLR3 agonist could be provided in an amount from about 10 pg/mL to about 100 mg/mL, but are preferably from about 1 µg/mL to about 1.5 µg/mL. Waterman 2010 reported the same protocol, and provided the TLR3 agonist at 1 µg/mL. The phenotype Waterman 2010 and the '787 publication refers to as an "immunosuppressive phenotype" is here referred to as an "anti-inflammatory" phenotype and MSCs having this phenotype are likewise sometimes referred to herein as "MSC2" cells.

Based on the results obtained with the TLR3 agonists reported in these references, it is expected that other TLR3 agonists could likewise be used in the inventive methods. TLR 3 agonists include IL4, IL13, polyadenosine:polyuracil (poly(A:U)), polyinosinic:polycytidylic acid (poly(I:C)), rintatolimid (see, e.g., Overton, et al., Vaccine 32(42):5490-95 (2014); Strayer et al., PLoS One. 2012; 7(3):e31334. doi: 10.1371/journal.pone.0031334)), an agonist called "RGC100" (Naumann et al., Clin Dev Immunol. 2013; 2013:283649. doi: 10.1155/2013/283649. Epub 2013 Dec. 2), double stranded RNA constructed to be a TLR3 agonist (see, International Patent Publication No. WO 2013/064584), derivatives of poly(I:C) designed to have better pharmacological properties, including those reported by Levy (J Infect Dis. 1975 October; 132(4):434-9), Bumcrot et al. (Nat Chem Biol. 2006 December; 2(12):711-9) and Basani et al. (Vaccine, 2009 27(25):3401-3404), and poly (C:G/I) (see, International Patent Publication Nos. WO 2013/064584 and WO 2015/091578). Each of these references is hereby incorporated by reference. Due to their common mechanism of action as an agonist of TLR3, each is expected to be effective in priming MSCs along an anti-inflammatory pathway.

In preferred embodiments of the inventive methods, the MSCs are incubated with a TLR3 agonist to prime the MSCs to have an anti-inflammatory phenotype. Preferably, the MSCs are incubated with one of more TLR3 agonists for 10 minutes to about 2 hours, more preferably 20 minutes to about 2 hours, still more preferably about 30 minutes to about 2 hours, about 30 minutes to about 1.5 hours, about 35 minutes to about 1.5 hour, about 40 minutes to about 1.5 hours, about 45 minutes to about 1.5 hour, about 50 minutes to about 70 minutes, or for about 46, 47, 48, 49, 50, 51, 52, 53, 54, 55, 56, 57, 58, 59, 60, 61, 62, 63, 64, 65, 66, 67, 68, 69 or 70 minutes, with the term "about" meaning ±2 minutes when referring to a range of minutes and ±30 seconds when referring to an individual number of minutes. The concentration of the TLR3 agonist can be any of the concentrations stated in the '787 publication, but is preferably about 1 µg/mL, with "about" in this context meaning ±0.5 µg/mL and more preferably ±0.2 µg/mL. The MSCs are then preferably washed twice. MSCs that have been incubated with a TLR3 agonist as described are considered to be primed, or polarized, along an anti-inflammatory pathway for purposes of the inventive methods and making the inventive devices.

H. Seeding MSCs onto Scaffolds and Incubation

In the inventive methods, MSCs are seeded on nanofiber meshwork scaffolds of a desired size and shape. In preferred embodiments, the MSCs have been primed to an anti-inflammatory phenotype, as described in the preceding section. The cells are preferably seeded at a density of 500,000/cm$^2$ to 1,500,000/cm$^2$, with a density of 500,000 to 750,000/cm$^2$ being preferred and 600,000/cm$^2$ more preferred. The cell-seeded scaffolds are then cultured under standard cell culture conditions. In a preferred embodiment, seeded scaffolds intended for use in humans are maintained in a humidified incubator at 37° C. and 5% $CO_2$. The seeded scaffolds are typically incubated in a medium supporting MSC proliferation. For example, the medium can be Minimum Essential Medium ("MEM") a medium, commercially available from, for example, Mediatech, Inc. (Manassas, Va.) or Biological Industries USA (Cromwell, Conn.), supplemented with 10% fetal bovine serum ("FBS"). The medium used in the studies reported in the Examples was MEM α, no nucleosides, (ThermoFisher Scientific Inc./Gibco™, Waltham, Mass.) supplemented with 10% FBS. For scaffolds intended for use in a non-human mammalian species, in which the incubation is of MSCs from that species, the incubation is preferably at the normal body temperature of that species. An incubation period is selected to allow time for the MSCs to proliferate and populate the scaffolds. The incubation period is typically at least 24 hours. It is also typically less than 168 hours as after a period of time the scaffold is adequately populated. Preferably, the incubation period is between about 24 hours to about 336 hours, and in some embodiments is about 24 hours to about 240 hours, in other embodiments is about 24 hours to about 168 hours, in other embodiments is about 24 hours to about 120 hours, in yet other embodiments is about 24 hours to about 120 hours, in still other embodiments is about 24 hours to about 96 hours, in other embodiments is about 24 hours to about 80 hours, in other embodiments is about 24 hours to about 72 hours, in some other embodiments is about 24 hours to about 60 hours, and in some embodiments is about 24 hours to about 50 hours, and in some embodiments is about 72 hours, with the term "about" in this context meaning ±1 hour of the stated period.

I. Decellularizing the Scaffolds

Following incubation, the seeded scaffolds are decellularized. A number of protocols and methods for decellularization are known and can be used in the methods of the invention. In a preferred embodiment, the decellularization is by repeated cycles of freezing, followed by thawing. In a particularly preferred embodiment, the freezing is in liquid nitrogen. In some preferred embodiments, the scaffolds are placed into a 3M NaCl solution while being thawed at room temperature (approximately 25° C.) after being frozen. Based on the results obtained in studies underlying the present disclosure, the scaffolds are preferably frozen 3-5 times, with 4 times being most preferred. Freezing in liquid nitrogen and thawing 6 or more times is not preferred as the repeated temperature cycling between is expected to be detrimental to the strength and integrity of the scaffolds.

J. Anti-Inflammatory Factors and Other Factors Present on the Scaffolds Following Decellularization Surprisingly, despite being subjected to multiple cycles of freezing in liquid nitrogen and thawing and multiple washes in a 3M NaCl solution between freezes, the scaffolds retained factors secreted by the MSCs during incubation or released by the MSCs during the decellularization process, or both. As set forth in the Examples, immunohistochemical studies performed to date showed the presence of the extracellular matrix protein fibronectin and of the anti-inflammatory factor IL-4 on the scaffolds. It is believed that additional ECM proteins, or anti-inflammatory factors, or both, are also likely to be secreted or released by the MSCs and present on the scaffolds and it is believed that these additional—but not yet defined—factors, in combination with those already shown to be present and the anti-inflammatory and pro-regenerative properties of chitosan in the scaffold, contribute to the ability of the inventive devices to provide robust recruitment of cells into the devices without inducing an inflammatory response. Accordingly, it is believed that the properties of the inventive devices cannot be reproduced by simply contacting a polymer/chitosan scaffold, or a PCL/CS scaffold, with fibronectin and IL-4.

EXAMPLES

Example 1

This Example discusses the tensile strength, elasticity and modulus of elasticity of an exemplar synthetic polymer, poly(caprolactone) ("PCL"), by itself and with various concentrations of chitosan.

Different blends of PCL and chitosan were studied for their physical properties. For comparison, two concentrations of PCL were studied by themselves. In brief, 6% PCL (based on the dry weight of PCL used, denoted as "wt %") was dissolved into a solvent of 95% hexafluoro isopropanol ("HFIP")/5% glacial acetic acid to form a solution, and PCL "coupons" were formed for testing. (For clarity, to make a 100 gram solution of 3 wt % PCL, 3 grams of PCL would be dissolved into 97 grams of HFIP solvent.) Blends of PCL and chitosan were made in the same manner. It was noted that even small amounts of chitosan made the solution viscous, and that a 6% PCL solution became too viscous for electrospinning so the percentage of PCL was cut in half, to 3%, with the intent of having solutions that could be used for electrospinning. Different percentages of chitosan, 5%, 10%, 15%, and 20% were blended into separate aliquots of 3% PCL in the solvent. (For clarity, the percentage of chitosan set forth presents the percentage of dry weight of chitosan used of the PCL present in the blend. To return to the hypothetical above, to make a blend stated to be 3% PCL and 10% chitosan, 0.30 grams of chitosan (10% of the 3 grams of PCL) would be dissolved into the solution.) The resulting blends were electrospun into sheets of approximately 250 μm thick and cut into tensile coupons or "dog bones" and tested on a MultiTest 5-i (Mecmesin Corp., Sterling, Va.) to determine their tensile strength, elongation, and modulus of elasticity.

The results of the studies are set forth in FIGS. 1-3. FIG. 1 shows the ultimate tensile strength ("UTS") in megaPascals (MPa) for 3 wt % and 6 wt % of PCL, and of 3 wt % PCL blended with 5%, 10%, 15%, and 20% chitosan. As can be seen in FIG. 1, the tensile strength of the polymer blend increased as the percentage of chitosan increased. Referring to FIG. 2, the elongation of the material (shown as percentages) is seen to decrease substantially as chitosan is introduced at 5%, and to continue to decrease as the percentage of chitosan in the blend increases. Elongation is measured as the extent to which the material could be stretched from its initial size before failure. A measurement of 100% elongation, for example, would indicate that the material was able to double in length before failure. FIG. 3 shows that the modulus of the material, shown in megaPascals, increases notably as the percentage of chitosan in the blend increases. The graph in each Figure shows the average value of five replicates for each composition.

Example 2

This Example sets forth the protocol used to prepare, seed, and incubate scaffolds used in the Examples reported below.

1) Preparation of scaffolds: Solutions of 3 wt % PCL/10% chitosan (compared to the PCL) was prepared. The solution was electrospun onto a rotating stainless steel rod through a 20 gauge blunt needle to form tubular scaffolds. Tubular scaffolds were placed in 700% ethanol for 30 minutes to sterilize them, washed 3× with sterile, deionized water and freeze-dried until use. The scaffolds made for the studies reported in the Examples were 3-10 mm long, with a diameter of 1-2 mm and were 400 microns thick.

2) Cell Culture of MSC2s on Tubular Scaffolds: MSC2s were prepared following the procedure of Waterman 2010, using poly(I:C) as the TLR3 agonist at a concentration of 1 µg/mL. The TLR3 agonist was added to the culture medium (MEM α, no nucleosides, ThermoFisher Scientific Inc./ Gibco™, Waltham, Mass., catalog no. 12561072, supplemented with 10% fetal bovine serum, pH 7.4), and the MSCs were then incubated for one hour. The culture medium with the poly(I:C) was then aspirated out and replaced with fresh culture medium. The primed MSCs, now considered MSC2s, were then seeded onto tubular PCL-CS scaffolds at 600,000/cm$^2$ in a sterile polypropylene cell culture tube and incubated on the PCL-CS scaffolds for 2-3 days in culture medium in the polypropylene tubes within a humidified incubator at 37° C. and 5% CO$^2$.

3) Freeze/thaw Decellularization: MSC2-seeded PCL-CS scaffolds were frozen in deionized water at −80° C. overnight or until use. The scaffolds were then thawed at room temperature and immediately placed in liquid nitrogen for 10 minutes, followed by an immediate immersion in a 37° C. 3M NaCl water bath for 10 minutes. This procedure was repeated twice. In other studies, a fourth freeze-thaw was added and the immersion in the 3M NaCl water bath was for 5 minutes, followed by an immersion for 5 minutes in pure distilled water. To reduce handling of the scaffolds while allowing ready submersion in the water baths and subsequent drainage, the steps described in this paragraph were performed while the scaffolds were contained in Micro processing/Embedded Cassettes (Electron Microscopy Sciences, Hatfield, Pa.).

4) Scanning Electron Microscopy ("SEM"): SEM studies were performed on some scaffolds. For these studies, samples were fixed with 10% formalin and then dehydrated in a graded ethanol (EtOH) series. The samples were mounted on SEM and sputter coated.

5) DAPI Staining: In some studies, samples were studied using DAPI staining. Samples for DAPI staining were fixed with 10% formalin and incubated in a 30 µM DAPI solution for 10 minutes at room temperature. The samples were then washed with phosphate buffer saline ("PBS") and studied by fluorescent imaging.

Example 3

This Example reports the results of studies conducted to determine if fibronectin was present on scaffolds following incubation with MSC2s.

Studies were conducted to visualize fibronectin presence on scaffolds by immunohistochemistry. PCL/chitosan scaffolds were seeded with MSC2s (primed with poly(I:C), as described in Example 2) at 600,000 cells/cm$^2$ and allowed to grow for 4 days. The scaffolds were then subjected to freeze/thaw decellularization and then washed to remove the cells and cellular debris. The scaffolds were then fixed with formalin and paraffin embedded. Cross sections of tissue (3-5 µm slices) were placed on a glass slide and analyzed via immunohistochemistry. Human anti-fibronectin antibody on the cross sectioned scaffolds was tagged and visualized using colorimetric IHC antibodies using peroxidase substrate reactions. Robust fibronectin signal was visualized over the entirely of the scaffolds, indicating strong deposition and retention of fibronectin on the scaffolds. The study was duplicated and the same results were obtained both times.

Fibronectin is the backbone ECM factor and has a number of Arg-Gly-Asp ("RGD") motifs which allow other ECM factors to adhere to the fibronectin and be retained on the scaffolds. The presence of fibronectin on the scaffolds following the freeze thaw procedure is therefore considered indicative that other ECM factors secreted by or released from the MSC2s are also present on the scaffolds following the freeze-thaw decellularization procedure. Fibronectin is also important for esophageal tissue construction as the esophagus has a considerable amount of fibronectin. It is thus expected that the presence of fibronectin will assist in recruiting esophageal precursor cells from surrounding tissue into the scaffolds when the scaffolds are implanted into subjects.

Example 4

This Example reports the results of studies conducted to determine if IL-4 was present on scaffolds following incubation with MSC2s. IL-4 is a prominent cytokine that decreases the production of Th1 cells and supports the up-regulation of Th2 cells. The presence of IL-4 promotes the activation of M2 macrophages, which is coupled with a secretion of IL-10 to result in a diminution of pathological inflammation, reducing fibrosis and promoting wound repair.

Studies were conducted to visualize IL-4 presence on scaffolds by immunohistochemistry, following the same methods described in the preceding example, but using human anti-IL4 antibodies in place of the anti-fibronectin antibodies. PCL/chitosan scaffolds were seeded with MSC2s at 600,000 cells/cm$^2$ and allowed to grow for 4 days. The scaffolds were then subjected to freeze/thaw decellularization and scaffolds were then washed to remove the cells and cellular debris. The scaffolds were then fixed with formalin and paraffin embedded. Cross sections of tissue (3-5 µm slices) were placed on a glass slide and analyzed via immunohistochemistry using anti-IL-4 antibodies. IL-4 signal was visualized over the entirely of the scaffolds, indicating deposition and retention of IL-4 on the scaffolds. The study was duplicated and the same results were obtained both times.

Example 5

This Example sets forth the results of studies to determine the effect of implanting the scaffolds made by the inventive methods in an animal model.

Decellularized scaffolds 3-4 mm long, 1-2 mm wide and 400 microns thick were prepared as described in Example 2, steps 1-3, and were sterilized under UV irradiation in a tissue culture hood for 30 minutes. Six immunocompetent mice each had one scaffold implanted into them. To avoid having to perform microsurgery to replace a portion of the esophagus or the intestine of the mice, each scaffold was wrapped around the fatty omentum of the mouse receiving it and placed near the mouse's intestine. It is noted that in use, the scaffold would be joined to the organ for which it was intended (such as the intestine or the esophagus) by surgical anastomosis and would not have a tissue, such as the omentum, physically separating the scaffold from the organ.

After 30 days, the animals were sacrificed. The area around each implant was shaved and the skin was examined for swelling or redness compared to the surrounding skin. No swelling or redness was noted around any of the implants. Each scaffold was removed, fixed with formalin to preserve any cells that had migrated onto or in the scaffold, and paraffin embedded. Cross sections of tissue (3-5 μm slices) were placed on a glass slide and analyzed by hematoxylin and eosin stain ("H&E") staining, which allowed observing the morphology of cells present on the scaffold, as well as their nuclei and cytoplasm. Study of the slides showed a large number of gastrointestinal cells, indicating robust recruitment of those cells onto the scaffolds. No signs of inflammation were seen (had they been present, they would have appeared as dense pockets of purple clusters), and few if any lymphocytes were present. If the scaffolds had provoked an inflammatory response, we would expect to have seen a substantial number of lymphocytes. These results suggest that the scaffolds did not provoke an inflammatory response.

Interestingly, although the scaffolds were wrapped in the omentum, which is a fatty tissue, most of the cells seen on the scaffolds were gastrointestinal cells, suggesting that the scaffolds preferentially recruited gastrointestinal cells rather than the fatty cells of the omentum.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. An implantable medical device for use in a mammal, comprising (a) a first scaffold comprising a meshwork of nanofibers of resorbable, non-toxic polymer and chitosan, and
    (b) IL-4 and fibronectin deposited in a spatial configuration on said first scaffold by isolated mesenchymal stem cells (MSCs) primed along an anti-inflammatory pathway, which primed MSCs have been (1) seeded on said first scaffold, (2) incubated on said first scaffold, and then (3) decellularized on said first scaffold, and wherein said primed MSCs have been primed along said anti-inflammatory pathway prior to or during said seeding of step (b)(1) or said incubation of step (b)(2), and wherein (i) said IL-4 and fibronectin are deposited on said first scaffold in amounts greater than IL-4 and fibronectin are deposited on a duplicate scaffold by MSCs seeded and incubated on said duplicate, first scaffold according to steps (b)(1)-(b)(3) but which have not been primed along an anti-inflammatory pathway, and (ii) said IL-4 and fibronectin are retained on said first scaffold in said spatial configuration in which said IL-4 and fibronectin were deposited by said primed MSCs.

2. The implantable medical device of claim 1, wherein said resorbable, non-toxic polymer is poly(caprolactone) ("PCL"), polyglycolide ("PGA"), poly(lactide-co-glycolide) ("PLGA"), polylactide-co-caprolactone ("PLCL"), polydioxanone ("PDO"), poly(3-hydroxybutyrate-co-3-hydroxyvalerate) ("PHBV"), poly((β-hydroxybutyrate) ("PHB"), polyanhydrides, poly trimethyl carbonate, poly (glycolide-co-trimethylene carbonate), (poly(lactic-co-glycolic acid), poly(glycolide-co-caprolactone), poly(DTH iminocarbonate), poly(bisphenol A iminocarbonate), polyurethane, polycyanoacrylate, and polyphosphazenepolycaprolactone, polylactic acid ("PLA"), or collagen.

3. The implantable medical device of claim 2, wherein said resorbable, non-toxic polymer is PCL, PGA, PLA, PLGA, PDO, trimethylene carbonate, or polyanhydride.

4. The implantable medical device of claim 2, wherein said resorbable, non-toxic polymer is PCL.

5. The implantable medical device of claim 1, wherein said MSCs have been primed along an anti-inflammatory pathway by incubating said isolated MSCs with a Toll-like receptor ("TLR") 3 agonist.

6. The implantable medical device of claim 5, wherein said TLR 3 agonist is IL4, IL13, polyadenosine:polyuracil (poly(A:U)), polyinosinic:polycytidylic acid (poly(I:C)), rintatolimid, RGC100, a double stranded RNA constructed to be an agonist of TLR3, a derivative of poly(I:C) that is an agonist of TLR3, and poly(C:G/I).

7. The implantable medical device of claim 6, wherein said TLR3 agonist is poly(I:C).

8. The implantable medical device of claim 1, wherein said nanofibers are electrospun.

9. The implantable medical device of claim 1, wherein said isolated MSCs are allogeneic.

10. The implantable medical device of claim 1, wherein said isolated MSCs are adipose-derived MSCs or bone-marrow-derived MSCs.

11. The implantable medical device of claim 1, wherein said mammal is a human and said isolated MSCs are allogeneic human MSCs.

12. A method for making an implantable medical device of a desired shape for use in a mammal, said implantable medical device bearing IL-4 and fibronectin from isolated mesenchymal stem cells ("MSCs") that have been primed along an anti-inflammatory pathway, in a spatial configuration on said device in which said IL-4 and fibronectin are deposited by said MSCs, and wherein said IL-4 and fibronectin are deposited on said implantable medical device in amounts larger than would be deposited on a duplicate of said implantable medical device by MSCs which have not been primed along said anti-inflammatory pathway,
    said method comprising the following steps, performed in the following order:
    (a) providing a first scaffold of a nanofiber meshwork in said desired shape, said nanofiber meshwork comprising nanofibers of a resorbable, non-toxic polymer and chitosan,
    (b) seeding said first scaffold with isolated MSCs,
    (c) incubating said isolated MSCs on said first scaffold, and
    (d) decellularizing said isolated MSCs on said first scaffold,
    wherein said MSCs have been primed along said anti-inflammatory pathway prior to or during said seeding of step (b) or said incubation of step (c), and wherein said IL-4 and fibronectin are retained on said scaffold in said spatial configuration in which said IL-4 and fibronectin were deposited by said primed MSCs, and in amounts larger than are deposited on a duplicate second scaffold by following steps (a)-(d) under the same conditions, but using MSCs which have not been primed along said anti-inflammatory pathway,
    thereby making said implantable medical device in said desired shape.

13. The method of claim 12, further wherein said decellularizing comprises freeze-thawing of said first scaffold seeded with said isolated MSCs.

14. The method of claim 12, further comprising step (e), lyophilizing said first scaffold following said decellularization.

15. The method of claim 12, further wherein said incubation of step (c) is for about 24 hours to about 240 hours.

16. The method of claim 15, further wherein said incubation of step (c) is for about 24 hours to about 96 hours.

17. The method of claim 12, wherein said MSCs are primed along said anti-inflammatory pathway by incubating said isolated MSCs with a Toll-like receptor ("TLR") 3 agonist.

18. The method of claim 17, wherein said TLR 3 agonist is IL4, IL13, polyadenosine:polyuracil (poly(A:U), polyinosinic:polycytidylic acid (poly(I:C)), rintatolimid, RGC100, a double stranded RNA that is an agonist of TLR3, a derivative of poly(I:C) that is an agonist of TLR3, and poly(C:G/I).

19. The method of claim 18, wherein said TLR3 ligand is poly(I:C).

20. The method of claim 12, wherein said nanofibers are electrospun.

21. The method of claim 12, wherein said isolated MSCs are allogeneic.

22. The method of claim 12, wherein said isolated MSCs are adipose-derived MSCs or bone-marrow-derived MSCs.

23. The method of claim 12, wherein said mammal is a human and said isolated MSCs are allogeneic human MSCs.

24. A method of treating a mammal in need thereof with an implantable medical device of a desired shape and size, said method comprising implanting into said mammal
a first nanofiber meshwork scaffold in said desired shape and size, said scaffold consisting of
(a) nanofibers of a resorbable, non-toxic polymer and chitosan, and
(b) IL-4 and fibronectin deposited in a spatial configuration on said first scaffold from isolated mesenchymal stem cells (MSCs) which have been primed along an anti-inflammatory pathway, which MSCs have been (1) seeded on said scaffold, (2) incubated on said scaffold, and then (3) decellularized on said scaffold, and wherein said MSCs are primed along said anti-inflammatory pathway either prior to or during said seeding or prior to or during said incubation on said first scaffold, and wherein said IL-4 and fibronectin are retained on said scaffold in said spatial configuration in which said ECM proteins were deposited by said MSCs, and in amounts larger than are deposited on a duplicate second scaffold following steps (b)(1)-(3), but using MSCs which have not been primed along said anti-inflammatory pathway,
thereby treating said mammal with said implantable medical device.

25. The method of claim 24, wherein said resorbable, non-toxic polymer is poly(caprolactone) ("PCL"), polyglycolide ("PGA"), poly(lactide-co-glycolide) ("PLGA"), polylactide-co-caprolactone ("PLCL"), polydioxanone ("PDO"), poly(3-hydroxybutyrate-co-3-hydroxyvalerate) ("PHB V"), poly((β-hydroxybutyrate) ("PHB"), polyanhydrides, poly trimethyl carbonate, poly (glycolide-co-trimethylene carbonate), (poly(lactic-co-glycolic acid), poly(glycolide-co-caprolactone), poly(DTH iminocarbonate), poly (bisphenol A iminocarbonate), polyurethane, polycyanoacrylate, and polyphosphazenepolycaprolactone, polylactic acid ("PLA"), or collagen.

26. The method of claim 25, wherein said resorbable, non-toxic polymer is PCL, PGA, PLA, PLGA, PDO, trimethylene carbonate, or polyanhydride.

27. The method of claim 25, wherein said resorbable, non-toxic polymer is PCL.

28. The method of claim 24, wherein said MSCs have been primed along an anti-inflammatory pathway by incubating said isolated MSCs with a Toll-like receptor ("TLR") 3 agonist.

29. The method of claim 24, wherein said TLR 3 agonist is IL4, IL13, polyadenosine:polyuracil (poly(A:U)), polyinosinic:polycytidylic acid (poly(I:C)), rintatolimid, RGC100, a double stranded RNA constructed to be an agonist of TLR3, a derivative of poly(I:C) that is an agonist of TLR3, and poly(C:G/I).

30. The method of claim 24, wherein said TLR3 agonist is poly(I:C).

31. The method of claim 24, wherein said nanofibers are electrospun.

32. The method of claim 24, wherein said isolated MSCs are allogeneic.

33. The method of claim 24, wherein said isolated MSCs are adipose-derived MSCs or bone-marrow-derived MSCs.

34. The method of claim 24, wherein said mammal is a human and said isolated MSCs are allogeneic human MSCs.

35. The implantable medical device of claim 1, further comprising one or more cytokines, cell growth factors, or extracellular matrix (ECM) proteins in addition to IL-4 and fibronectin deposited in a spatial configuration on said scaffold by said MSCs, and wherein said cytokines, cell growth factors, or ECM proteins in addition to IL-4 and fibronectin are retained on said scaffold in said spatial configuration in which said cytokines, cell growth factors, or ECM proteins in addition to IL-4 and fibronectin were deposited by said MSCs.

36. The method of claim 24, further wherein said scaffold comprises one or more cytokines, cell growth factors, or extracellular matrix (ECM) proteins in addition to IL-4 and fibronectin deposited in a spatial configuration on said scaffold by said MSCs, and wherein said one or more cytokines, cell growth factors, or ECM proteins in addition to IL-4 are retained on said scaffold in said spatial configuration in which said cytokines, cell growth factors, or ECM proteins in addition to IL-4 were deposited by said MSCs.

* * * * *